United States Patent
Funk et al.

(10) Patent No.: US 6,472,478 B1
(45) Date of Patent: Oct. 29, 2002

(54) PROCESS FOR CROSSLINKING HYDROGELS WITH BIS- AND POLY-2-OXAZOLIDINONES

(75) Inventors: Rüdiger Funk, Niedernhausen; Volker Frenz, Mainz-Kostheim; Ulrich Riegel, Frankfurt; Matthias Weismantel, Jossgrund-Oberndorf, all of (DE); Fritz Engelhardt; Thomas Daniel, both of Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/601,349
(22) PCT Filed: Feb. 19, 1999
(86) PCT No.: PCT/EP99/01087
§ 371 (c)(1), (2), (4) Date: Aug. 18, 2000
(87) PCT Pub. No.: WO99/42494
PCT Pub. Date: Aug. 26, 1999

(30) Foreign Application Priority Data

Feb. 21, 1998 (DE) .......................... 198 07 502

(51) Int. Cl.⁷ .......................... C08F 8/30; A61L 15/00
(52) U.S. Cl. .................. 525/327.6; 525/329.9; 525/375; 524/556; 524/916; 442/417; 604/367
(58) Field of Search .................. 525/329.9, 375, 525/327.6; 524/916, 556; 442/417; 604/367

(56) References Cited

U.S. PATENT DOCUMENTS

| | | |
|---|---|---|
| 3,364,181 A | 1/1968 | Elder et al. |
| 3,367,942 A | 2/1968 | Hickner |
| 3,635,835 A | 1/1972 | Peterson |
| 3,965,072 A | 6/1976 | Markiewitz |
| 4,056,502 A | 11/1977 | Gross |
| 4,076,917 A | 2/1978 | Swift et al. |
| 4,101,606 A | 7/1978 | Cenci et al. |
| 4,115,637 A | 9/1978 | Cenci et al. |
| 4,123,419 A | 10/1978 | Heiss et al. |
| 4,138,541 A | 2/1979 | Cenci et al. |
| 4,203,900 A | 5/1980 | Kaiser |
| 4,209,607 A | 6/1980 | Shalaby et al. |
| 4,293,669 A | 10/1981 | Rottmaier et al. |
| 4,443,490 A | 4/1984 | Nakajima et al. |
| 4,482,659 A | 11/1984 | Sanjana et al. |
| 4,608,419 A | 8/1986 | Dorman et al. |
| 4,626,575 A | 12/1986 | Goel |
| 4,666,983 A | 5/1987 | Tsubakimoto et al. |
| 4,677,167 A | 6/1987 | Goel |
| 4,705,885 A | 11/1987 | Just et al. |
| 4,708,984 A | 11/1987 | Forigone et al. |
| 4,727,111 A | 2/1988 | Pettit, Jr. et al. |
| 4,761,457 A | 8/1988 | Arita et al. |
| 4,785,070 A | 11/1988 | Rasmussen et al. |
| 4,788,255 A | 11/1988 | Pettit, Jr. et al. |
| 4,801,680 A | 1/1989 | Geary et al. |
| 4,889,890 A | 12/1989 | Kerr et al. |
| 4,937,288 A | 6/1990 | Pettit, Jr. et al. |
| 4,988,767 A | 1/1991 | Pettit, Jr. |
| 4,990,579 A | 2/1991 | Paar |
| 5,006,622 A | 4/1991 | Kunzler et al. |
| 5,013,791 A | 5/1991 | Kerr et al. |
| 5,019,606 A | 5/1991 | Marten et al. |
| 5,039,759 A | 8/1991 | Hoy et al. |
| 5,098,955 A | 3/1992 | Pettit, Jr. |
| 5,124,421 A | 6/1992 | Ulbrich et al. |
| 5,130,479 A | 7/1992 | Ulbrich et al. |
| 5,143,582 A | 9/1992 | Arkens et al. |
| 5,182,337 A | 1/1993 | Pettit, Jr. et al. |
| 5,214,101 A | 5/1993 | Pettit, Jr. et al. |
| 5,266,628 A | 11/1993 | Essary et al. |
| 5,292,807 A | 3/1994 | Shaefer et al. |

(List continued on next page.)

FOREIGN PATENT DOCUMENTS

| | | |
|---|---|---|
| EP | 0 083 022 | 7/1983 |
| EP | 0 349 935 | 1/1990 |
| EP | 0 372 981 | 6/1990 |
| EP | 0 530 438 | 3/1993 |
| EP | 0 543 303 | 5/1993 |

OTHER PUBLICATIONS

D.L. Trumbo, Polymer Bulletin, vol. 31, pp. 637–643, "Polymers Form 2–Oxazolidone and Dicarbonxylic Acids," 1993.

Primary Examiner—D. R. Wilson
(74) Attorney, Agent, or Firm—Oblon, Spivak, McClelland, Maier & Neustadt, P.C.

(57) ABSTRACT

The invention relates to a process for the gel or surface postcrosslinking of water-absorbing polymers in which the polymers are treated with a surface postcrosslinking solution and during or after the treatment are postcrosslinked and dried by means of an increase in temperature, the crosslinker being a compound of the formula

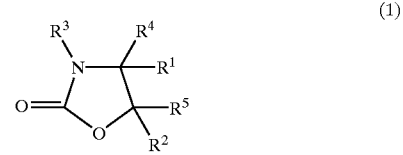

(1)

in which $R^1$ and $R^2$ independently of one another are H, hydroxyl, phenyl or $C_1$–$C_6$-alkyl, $R^3$ is hydrogen, $C_1$–$C_{12}$-alkyl, $C_1$–$C_{12}$-alkenyl or $C_6$–$C_{12}$-aryl and $R^4$ and $R^5$ independently of one another are $C_{1-C12}$-alkyl, $C_{1-C12}$-alkenyl, $C_{6-C12}$-aryl, hydroxyl, $C_{1-C12}$-alkoxy or hydrogen, dissolved in an inert solvent, to water-absorbing polymers which can be obtained by said process, and to their use in hygiene articles, packaging materials and nonwovens.

15 Claims, No Drawings

U.S. PATENT DOCUMENTS

| | | |
|---|---|---|
| 5,318,990 A | 6/1994 | Strauss |
| 5,331,059 A | 7/1994 | Engelhardt et al. |
| 5,340,868 A | 8/1994 | Strauss et al. |
| 5,346,947 A | 9/1994 | Guerro et al. |
| 5,360,876 A | 11/1994 | Burgoyne, Jr. et al. |
| 5,385,983 A | 1/1995 | Graham |
| 5,395,911 A | 3/1995 | Frings et al. |
| 5,427,587 A | 6/1995 | Arkens et al. |
| 5,536,766 A | 7/1996 | Seyffer et al. |
| 5,840,822 A | 11/1998 | Lee et al. |
| 6,140,388 A * | 10/2000 | Nass et al. .................. 523/139 |
| 6,297,335 B1 * | 10/2001 | Funk et al. .............. 526/317.1 |

* cited by examiner

PROCESS FOR CROSSLINKING HYDROGELS WITH BIS- AND POLY-2-OXAZOLIDINONES

The present invention relates to a process for the gel or surface postcrosslinking of water-absorbing hydrogels by copolymerization with 2-oxazolidinones, to the polymers obtainable in this way and to their use in hygiene articles, packaging materials and nonwovens.

Hydrophilic highly swellable hydrogels are, in particular, polymers composed of (co)polymerized hydrophilic monomers, or are graft (co)polymers of one or more hydrophilic monomers on a suitable graft base, crosslinked cellulose ethers or crosslinked starch ethers, crosslinked carboxymethylcellulose, partially crosslinked polyalkylene oxide, or natural products that are swellable in aqueous liquids: guar derivatives, for example. Hydrogels of this kind are used as products for absorbing aqueous solutions in the production of diapers, tampons, sanitary towels and other hygiene articles, and as water retainers in market gardening.

To improve service properties such as diaper rewet and AUL, for example, hydrbphilic highly swellable hydrogels are generally subjected to surface or gel postcrosslinking. This postcrosslinking is known to the person skilled in the art and is preferably carried out in the aqueous gel phase or as surface postcrosslinking of the milled and sieved polymer particles.

Crosslinkers suitable for this purpose are compounds comprising at least two groups which are able to form covalent bonds with the carboxyl groups of the hydrophilic polymer. Examples of suitable crosslinkers are diglycidyl or polyglycidyl compounds, such as diglycidyl phosphonate, alkoxysilyl compounds, polyaziridines, polyamines and polyamidoamines, and these compounds can also be used in mixtures with one another (see for example EP-A-0 083 022, EP-A-0 543 303 and EP-A-0 530 438). Polyamidoamines which are suitable as crosslinkers are described in particular in EP-A-0 349 935.

A major disadvantage of these crosslinkers is their high reactivity, since it necessitates the taking of special protective measures in the production plant in order to avoid unwanted side effects. In addition, the abovementioned crosslinkers possess skin-irritant properties, which appears problematic in their use in hygiene articles.

Polyfunctional alcohols are also known crosslinkers. For example, EP-A-0 372 981, U.S. Pat. No. 4,666,983 and U.S. Pat. No. 5,385,983 teach the use of hydrophilic polyalcohols and the use of polyhydroxy surfactants. According to these documents the reaction is carried out at temperatures of 120–250° C. The process has the disadvantage that the esterification reaction which leads to crosslinking is slow even at such temperatures.

The object was therefore, using compounds which are relatively slow to react yet are reactive with carboxyl groups, to achieve just as good if not better gel or surface postcrosslinking. This object is to be achieved with a very short reaction time and a very low reaction temperature. Ideally, the prevailing reaction conditions should be the same as those obtaining when highly reactive epoxides are used.

It has surprisingly now been found that this object can be achieved to outstanding effect with 2-oxazolidinones as crosslinkers. In particular, the moderate reactivity of these crosslinkers can be increased by adding organic or inorganic acidic catalysts. Suitable catalysts are the known inorganic mineral acids, their acidic salts with alkali metals or with ammonium, and their anhydrides. Suitable organic catalysts are the known carboxylic, sulfonic and amino acids.

The invention provides a process for the gel or surface postcrosslinking of water-absorbing polymers in which the polymers are treated with a surface postcrosslinking solution and during or after the treatment are postcrosslinked and dried by means of an increase in temperature, if the rosslinker is a compound of the formula

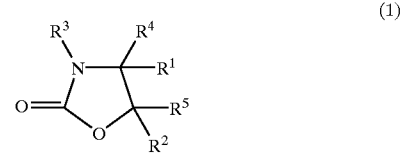

(1)

in which $R^1$ and $R^2$ independently of one another are H, hydroxyl, phenyl or $C_1$–$C_6$-alkyl, $R^3$ is hydrogen, $C_1$–$C_{12}$-alkyl, N-hydroxy-($C_2$–$C_6$)-alkyl, $C_1$–$C_{12}$-alkenyl or $C_6$–$C_{12}$-aryl and $R^4$ and $R^5$ independently of one another are $C_1$–$C_{12}$-alkyl, $C_1$–$C_{12}$-alkenyl, $C_6$–$C_{12}$-aryl, hydroxyl, $C_1$–$C_{12}$-alkoxy or hydrogen, dissolved in an inert solvent. Examples of preferred and suitable crosslinkers of this type are 2-oxazolidinone, N-methyl-2-oxazolidinone and N-hydroxyethyl-2-oxazolidinone.

The preferred temperature range for postcrosslinking and drying is that between 50 and 250° C., in particular 50–200° C. and, with particular preference, the range between 100–180° C. The surface postcrosslinking solution is preferably applied to the polymer by spraying in suitable spray mixers. Following spray application, the polymer powder is dried thermally, it being possible for the crosslinking reaction to take place either before or during drying. Preference is given to the spray application of a solution of the crosslinker in reaction mixers or mixing and drying systems, such as Lödige mixers, BEPEX mixers, NAUTA mixers, SHUGGI mixers or PROCESSALL apparatus. It is, moreover, also possible to employ fluidized-bed dryers.

Drying can take place in the mixer itself, by heating the outer casing or by blowing in hot air. Likewise suitable is a downstream dryer, such as a shelf dryer, a rotary dryer or a heatable screw. Alternatively, azeotropic distillation, for example, can be utilized as a drying technique. The preferred residence time at this temperature in the reaction mixer or dryer is less than 30 minutes, with particular preference less than 10 minutes.

In one preferred embodiment of the invention the reaction is accelerated by adding an acidic catalyst to the surface postcrosslinking solution. Catalysts which can be used in the process of the invention are all inorganic acids, their anhydrides, and organic acids. Examples are boric, sulfuric, hydroiodic, phosphoric, tartaric, acetic and toluenesulfonic acid. Also suitable in particular are their polymeric forms, anhydrides, and the acid salts of the polybasic acids. Examples thereof are boron oxide, sulfur trioxide, diphosphorus pentoxide, and ammonium dihydrogen phosphate.

The crosslinker is dissolved in inert solvents. The crosslinker is used in an amount of from 0.01–1.0% by weight based on the polymer employed. As an inert solvent, preference is given to water and to mixtures of water with monohydric or polyhydric alcohols. It is, however, possible to employ any organic solvent of unlimited miscibility with water which is not itself reactive under the process conditions. Where an alcohol/water mixture is employed the alcohol content of this solution is, for example, 10–90% by weight, preferably 30–70% by weight, in particular 40–60% by weight. Any alcohol of unlimited miscibility with water can be employed, as can mixtures of two or more alcohols (e.g. methanol+glycerol+water). The alcohol mixtures may comprise the alcohols in any desired mixing ratio. Particular preference is given to the use of the following alcohols in aqueous solution: methanol, ethanol, isopropanol, ethylene glycol and, with particular preference, 1,2-propanediol and also 1,3-propanediol.

In another preferred embodiment of the invention the surface postcrosslinking solution is employed in a proportion of 1–20% by weight based on the mass of the polymer. Particular preference is given to an amount of solution of 2.5–15% by weight based on the polymer.

The invention additionally provides crosslinked water-absorbing polymers which are obtainable by the process of the invention.

The hydrophilic highly swellable hydrogels to be employed in the process of the invention are in particular, polymers composed of (co)polymerized hydrophilic monomers, or are graft (co)polymers of one or more hydrophilic monomers on a suitable graft base, crosslinked cellulose ethers or crosslinked starch ethers, or natural products which are swellable in aqueous liquids: guar derivatives, for example. These hydrogels are known to the person skilled in the art and are described, for example, in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A-26 12 846, DE-A-40 20 780, EP-A-0 205 674, U.S. Pat. No. 5,145,906, EP-A-0 530 438, EP-A-0 670 073, U.S. Pat. No. 4,057,521, U.S. Pat. No. 4,062,817, U.S. Pat. No. 5,255,527, U.S. Pat. No. 295,987, U.S. Pat. No. 5,011,892, U.S. Pat. No. 4,076,663 and U.S. Pat. No. 931,497. The content of the abovementioned patent documents is expressly incorporated into the present disclosure by reference. Examples of hydrophilic monomers suitable for preparing these hydrophilic highly swellable hydrogels are polymerizable acids, such as acrylic acid, methacrylic acid, vinylsulfonic acid, vinylphosphonic acid, maleic acid including its anhydride, fumaric acid, itaconic acid, 2-acrylamido-2-methylpropanesulfonic acid, 2-acrylamido-2-methylpropanephosphonic acid, and also their amides, hydroxyalkyl esters, and amino- or ammonium-functional esters and amides and also the alkali metal and/or ammonium salts of monomers containing acid groups. Also suitable, furthermore, are water-soluble N-vinyl amides such as N-vinylformamide or diallyidimethylammonium chloride. Preferred hydrophilic monomers are compounds of the formula

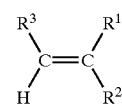

(2)

in which
R$^1$ is hydrogen, methyl or ethyl,
R$^2$ is —COOR$^4$, a sulfonyl group, a phosphonyl group, a (C$_{1-C_4}$)-alkanol-esterified phosphonyl group, or a group of the formula

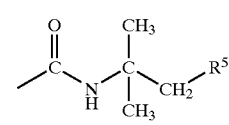

(3)

in which
R$^3$ is hydrogen, methyl, ethyl or a carboxyl group,
R$^4$ is hydrogen, amino-(C$_1$–C$_4$)-alkyl, hydroxy-(C$_1$–C$_4$)-alkyl, an alkali metal ion or ammonium ion, and
R$^5$ is a sulfonyl group, a phosphonyl group, a carboxyl group or the alkali metal or ammonium salts of each of these groups.

Examples of (C$_1$–C$_4$)-alkanols are methanol, ethanol, n-propanol, isopropanol and n-butanol.

Particularly preferred hydrophilic monomers are acrylic and methacrylic acid and alkali metal or ammonium salts thereof, for example sodium acrylate, potassium acrylate or ammonium acrylate.

Suitable graft bases for hydrophilic hydrogels obtainable by graft copolymerization of olefinically unsaturated acids or their alkali metal or ammonium salts may be natural or synthetic in origin. Examples are starch, cellulose and cellulose derivatives, and also other polysaccharides and oligosaccharides, polyalkylene oxides, especially polyethylene oxides and polypropylene oxides, and hydrophilic polyesters.

Suitable polyalkylene oxides have, for example, the formula

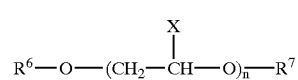

(4)

in which
R$^6$ and R$^7$ independently of one another are hydrogen, alkyl, alkenyl, phenyl or acyl,
X is hydrogen or methyl, and
n is an integer from 1 to 10,000.
R$^6$ and R$^7$ are preferably hydrogen, (C$_1$–C$_4$)-alkyl, (C$_2$–C$_6$)-alkenyl or phenyl.

Particularly preferred hydrogels are polyacrylates, polymethacrylates, and the graft copolymers described in U.S. Pat. No. 4,931,497, U.S. Pat. No. 5,011,892 and U.S. Pat. No. 5,041,496.

The hydrophilic highly soluble hydrogels are preferably in crosslinked form; that is, they include compounds having at least two double bonds which have been copolymerized into the polymer network. Particularly suitable crosslinkers are N,N'-methylenebisacrylamide and N,N'-methylenebismethacrylamide, esters of unsaturated mono- or polycarboxylic acids with polyols, such as diacrylate or triacrylate, examples being the diacrylates and dimethacrylates of butanediol and of ethylene glycol, and trimethylolpropane triacrylate, and also allyl compounds such as allyl (meth) acrylate, triallyl cyanurate, diallyl maleate, polyallyl esters, tetraallyoxyethane, triallylamine, tetraallylethylenediamine, allyl esters of phosphoric acid, and vinylphosphonic acid derivatives as described, for example, in EP-A-0 343 427. In the process of the invention, however, particular preference is given to hydrogels prepared using polyallyl ethers as crosslinkers and by acidic homopolymerization of acrylic acid. Suitable crosslinkers are pentaerythritol tri- and tetraallyl ether, polyethylene glycol crosslinkers are pentaerythritol tri- and tetraallyl ether, polyethylene glycol diallyl ether, monoethylene glycol diallyl ether, glycerol di- and triallyl ether, polyallyl ethers based on sorbitol, and ethoxylated variants thereof.

The water-absorbing polymer is preferably a polymeric acrylic acid or a polyacrylate. The preparation of this water-absorbing polymer can be carried out by a process known from the literature. Preferred polymers are those comprising crosslinking comonomers (for example, in amounts of 0.001–10, preferably 0.01–1, mol %). However, very particular preference is given to polymers obtained by free-radical addition polymerization using a polyfunctional ethylenically unsaturated free-radical crosslinker which additionally carries at least one free hydroxyl group (such as pentaerythritol triallyl ether or trimethylolpropane diallyl ether).

The hydrophilic highly swellable hydrogels can be prepared by conventional polymerization processes. Preference is given to addition polymerization in aqueous solution by the process known as gel polymerization. In this process, for example, from 15 to 50% by weight strength aqueous solutions of one or more hydrophilic monomers, and, if desired, of a suitable graft base, are polymerized in the presence of a free-radical initiator, preferably without mechanical mixing, utilizing the Trommsdorff-Norrish effect (Makromol. Chem. 1 (1947) 169). The polymerization reaction can be conducted in the temperature range between 0° C. and 150° C., preferably between 10° C. and 100° C., either at atmospheric pressure or under an increased or reduced pressure. As is usual, the polymerization may also be performed in an inert gas atmosphere, preferably under nitrogen. The polymerization can be initiated using high-energy electromagnetic radiation or by the customary chemical polymerization initiators. Examples of the latter are organic peroxides, such as benzoyl peroxide, tert-butyl hydroperoxide, methyl ethyl ketone peroxide and cumene hydroperoxide, azo compounds, such as azodiisobutyronitrile, and inorganic peroxo compounds, such as $(NH_4)_2S_2O_8$, $K_2S_2O_8$ and $H_2O_2$. These can if desired be used in combination with reducing agents such as sodium hydrogen sulfite or iron(II) sulfate, or redox systems. Redox systems include a reducing component, which is generally an aliphatic or aromatic sulfinic acid, such as benzenesulfinic acid or toluenesulfinic acid or derivatives of these acids, such as Mannich adducts of sulfinic acids, of aldehydes or amino compounds as described in DE-C-1 301 566.

The qualities of the polymers can be improved further by continuing to heat the polymer gels for a number of hours within the temperature range from 50 to 130° C., preferably from 70 to 100° C.

The resultant gels are neutralized, for example, to the extent of 0–100 mol % based on monomer employed, preferably 25–100 mol % and with particular preference 50–85 mol %, it being possible to use the customary neutralizing agents, preferably alkali metal hydroxides or alkali metal oxides, and with particular preference sodium hydroxide, sodium carbonate or sodium hydrogen carbonate.

Neutralization is usually effected by mixing in the neutralizing agent as an aqueous solution or else, preferably, as a solid. For this purpose the gel is mechanically comminuted, by means of a mincer for example, and the neutralizing agent is sprayed on, scattered over or poured on, and then carefully mixed in. To effect homogenization the resultant gel mass may be passed through the mincer again a number of times. The neutralized gel mass is then dried with a belt dryer or roll dryer until the residual moisture content is preferably less than 10% by weight, in particular below 5% by weight. The dried hydrogel is then ground and sieved, the usual grinding apparatus being roll mills, pin mills or vibrator mills. The preferred particle size of the sieved hydrogel lies in the range 45–1000 µm, with particular preference 45–850 µm and with very particular preference 200–850 µm.

In order to ascertain the quality of surface postcrosslinking the dried hydrogel is then tested using the test methods described below:

Methods:

1) Centrifuge Retention Capacity (CRC):

This method measures the free swellability of the hydrogel in a teabag. Approximately 0.200 g of dry hydrogel are sealed into a teabag (format: 60 mm×60 mm, Dexter 1234T paper) and soaked for 30 minutes in 0.9% strength by weight sodium chloride solution. The teabag is then spun for 3 minutes in a customary commercial spindryer (Bauknecht WS 130, 1400 rpm, basket diameter 230 mm). The amount of liquid absorbed is determined by weighing the centrifuged teabag. The absorption capacity of the teabag itself is taken into account by determination of a blank value (teabag without hydrogel), which is deducted from the weighing result (teabag with swollen hydrogel).

Retention CRC [g/g]=(weighing result teabag—blank value—initial weight of hydrogel)/initial weight of hydrogel 2) Absorbency Under Load (0.3/0.5/0.7 psi):

For the absorbency under load, 0.900 g of dry hydrogel is distributed uniformly on the screen base of a measuring cell. The measuring cell consists of a Plexiglas cylinder (height= 50 mm, diameter=60 mm) whose base is formed by sticking on a screen of steel mesh (mesh size 36 microns, or 400 mesh). A cover plate is placed over the uniformly distributed hydrogel and loaded with an appropriate weight. The cell is then placed on a filter paper (S&S 589 black band, diameter=90 mm) lying on a porous glass filter plate, this filter plate itself lying in a Petri dish (height=30 mm, diameter=200 mm) which contains 0.9% strength by weight sodium chloride solution so that the liquid level at the beginning of the experiment is level with the top edge of the glass frit. The hydrogel is then left to absorb the salt solution for 60 minutes. Subsequently, the complete cell with the swollen gel is removed from the filter plate and the apparatus is reweighed following removal of the weight.

The absorbency under load (AUL) is calculated as follows:

$$AUL[g/g]=(Wb-Wa)/Ws$$

where

Wb is the mass of the apparatus+gel after swelling,

Wa is the mass of the apparatus+initial weight of gel before swelling, and

Ws is the initial weight of dry hydrogel.

The apparatus consists of measuring cylinder and cover plate.

EXAMPLE 1

In a 40 l plastic bucket, 6.9 kg of pure acrylic acid are diluted with 23 kg of water. 45 g of pentaerythritol triallyl ether are added with stirring to this solution, and the sealed bucket is rendered inert by passing nitrogen through it. The polymerization is then initiated by adding about 400 mg of hydrogen peroxide and 200 mg of ascorbic acid. After the end of the reaction the gel is mechanically comminuted and sodium hydroxide solution is added in an amount sufficient to achieve a degree of neutralization of 75 mol %, based on the acrylic acid employed. The neutralized gel is then dried on a roll dryer, ground with a pin mill and, finally, isolated by sieving. This is the base polymer used in the subsequent examples.

The base polymer in a Waring laboratory mixer is sprayed with a crosslinker solution in such an amount that 5% methanol, 5% water and 0.20% 2-oxazolidinone, based on polymer employed, are used. Subsequently, a portion of the moist product is treated at 170° C. for 60 minutes and the remainder at 170° C. for 90 minutes, in a circulating air drying cabinet. The dried product is isolated by sieving at 850 microns in order to remove lumps.

EXAMPLE 2

Base polymer prepared as in Example 1 is sprayed with crosslinker solution in a Waring laboratory mixer. In this case the solution has a composition such that the following dosing is achieved, based on base polymer employed: 0.20% by weight 2-oxazolidinone, 5% by weight propylene glycol and 5% by weight water. The moist polymer is then dried at 175° C. for 40 and 60 minutes respectively.

EXAMPLE 3

Base polymer prepared as in Example 1 is sprayed with crosslinker solution in a Waring laboratory mixer. In this case the solution has a composition such that the following dosing is achieved, based on base polymer employed: 0.20% by weight 2-oxazolidinone, 5% by weight propylene glycol, 5% by weight water and 0.2% by weight boric acid. The moist polymer is then dried at 175° C. for 30 minutes.

EXAMPLE 4

Base polymer prepared as in Example 1 is sprayed with crosslinker solution in a Waring laboratory mixer. In this case the solution has a composition such that the following dosing is achieved, based on base polymer employed: 0.20% by weight 2-oxazolidinone, 5% by weight propylene glycol, 5% by weight water and 0.2% by weight ammonium dihydrogen phosphate. The moist polymer is then dried at 175° C. for 30 minutes.

The surface-postcrosslinked polymers prepared in accordance with the above examples were tested as described above. The results are summarized in the table below:

Drying temperature and drying time here relate to the heat treatment of the base polymer sprayed with surface-postcrosslinking solution.

TABLE

| Polymer | Drying temperature | Drying time | Catalyst | Solvent | CRC [g/g] | AUL 0.3 psi [g/g] | AUL 0.7 psi- (4826.5 Pa) [g/g] |
|---|---|---|---|---|---|---|---|
| Base polymer (prepared as in Example 1) Postcrosslinking according to: | — | — | — | — | 42 | 10 | 9 |
| Example 1 | 170° C. | 60 min | — | Methanol/water | 35 | 36 | 21 |
| Example 1 | 170° C. | 90 min | — | Methanol/water | 32 | 34 | 27 |
| Example 2 | 175° C. | 40 min | — | Propylene glycol/water | 35 | 35 | 27 |
| Example 2 | 175° C. | 60 min | — | Propylene glycol/water | 34 | 33 | 25 |
| Example 3 | 175° C. | 30 min | 0.2% $H_3BO_3$ | Propylene glycol/water | 32 | 31 | 25 |
| Example 4 | 175° C. | 30 min | 0.2% $NH_4H_2PO_4$ | Propylene glycol/water | 31 | 30 | 24 |

EXAMPLE 5a

Base polymer prepared as in Example 1 is sprayed with crosslinker solution in a ®Shuggi Contactor. In this case the solution has a composition such that, based on base polymer employed, the following dosing is achieved: 0.20% by weight 2-oxazolidinone, 2% by weight propylene glycol and 3% by weight water. The moist polymer is conveyed directly from the Contactor into a toroidal disk dryer in which it is dried at 185° C. (product discharge temperature) for a residence time of 35 minutes. The resulting product is screened to remove the oversize (>850 microns), after which it has the following product data: CRC=27 g/g; AUL 0.7 psi=25 g/g.

EXAMPLE 5b

In an entirely analogous manner and using the same equipment, a sample 5b was prepared with the following crosslinker solution: 4% by weight propylene glycol, 6% by weight water, 0.20% by weight 2-oxazolidinone and 0.10% by weight $Al_2(SO_4)_3$ 12–14 $H_2O$. The product was dried at 175° C. (product discharge temperature) for a residence time of 35 minutes. The resulting product was screened to remove the oversize (>850 microns), after which it had the following product data: CRC=31 g/g; AUL 0.7 psi=25 g/g.

EXAMPLE 6

Base polymer prepared as in Example 1 is sprayed with crosslinker solution in a ®Shuggi Contactor. In this case the solution has a composition such that, based on base polymer employed, the following dosing is achieved: 0.10% by weight 2-oxazolidinone, 3% by weight methanol and 7% by weight water. The moist polymer is dried in a ®Nara paddle dryer at 185° C. (product discharge temperature) for a residence time of 45 minutes. The resulting product is screened to remove the oversize (>850 microns), after which it has the following product data: CRC=26 g/g; AUL 0.7 psi=25 g/g.

EXAMPLE 7a

Base polymer prepared as in Example 1 is sprayed with crosslinker solution in a laboratory plowshare mixer (®ProcessAl). In this case the solution has a composition such that the following dosing is achieved based on base polymer employed: 0.20% by weight 2-oxazolidinone, 4% by weight 1,2-propanediol, 6% by weight water and 0.10% by weight boric acid. The moist polymer is dried in a pilot-plant fluidized-bed dryer (®Carman Fluidized Bed Dryer) at 200° C. (fluidized-bed temperature) for a residence time of 10 minutes. The resulting product is screened to remove the oversize (>850 microns), after which it has the following product data: CRC=29 g/g; AUL 0.7 psi=25 g/g.

EXAMPLE 7b

A product prepared in an entirely analogous manner and dried at 190° C. with a residence time of 9 minutes was screened to remove the oversize (>850 microns), after which it had the following product data: CRC=33g/g; AUL 0.7 psi=26 g/g.

We claim:

1. A process for the gel or surface postcrosslinking of water-absorbing polymers, comprising; treating polymers with a surface postcrosslinking solution containing a crosslinker, and postcrosslinking and drying by means of an increase in temperature, wherein said crosslinker is a compound of the formula

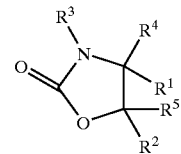

(1)

in which $R^1$ and $R^2$ independently of one another are H, hydroxyl, phenyl or $C_1$–$C_6$-alkyl, $R^3$ is hydrogen, $C_1$–$C_{12}$-alkyl, N-hydroxy-($C_2$–$C_6$)-alkyl, $C_1$–$C_{12}$-alkenyl or $C_6$–$C_{12}$-aryl and $R^4$ a $R^5$ independently of one another are $C_1$–$C_{12}$-alkoxy or hydrogen, dissolved in an inert solvent.

2. The process as claimed in claim 1, wherein surface postcrosslinking occurs during or after treatment of the gel or surface with said postcrosslinking solution.

3. The process as claimed in claim 1, wherein said crosslinker is selected from the group consisting of 2-oxazolidinone, N-methyl-2-oxazolidinone, and N-hydroxyethyl-2-oxazolidinone.

4. The process as claimed in claim 1, wherein the water-absorbing polymer is selected from the group consisting of a polymeric acrylic acid, and a polyacrylate.

5. The process as claimed in claim 1, wherein said water-absorbing polymer is a polymeric acrylic acid or polyacrylate obtained by free-radical addition polymerization using a polyfunctional ethylenically unsaturated free-radical crosslinker which may additionally carry one or more free hydroxyl groups.

6. The process as claimed in claim 1, wherein said surface postcrosslinking solution further comprises a catalyst used for crosslinking, wherein said catalyst is an inorganic acid, an inorganic acid anhydride, an organic acid, or an organic acid anhydride.

7. The process as claimed in claim 6, wherein said catalyst is boric acid, sulfuric acid, hydroiodic acid, phosphoric acid, tartaric acid, acetic acid, toluenesulfonic acid, or the polymeric form, anhydride or acid salt thereof.

8. The process as claimed in claim 1, wherein said inert solvent is selected from the group consisting of water, a mixture of water with organic solvents of unlimited solubility in water, and a mixture of water with monohydric or polyhydric alcohols.

9. The process as claimed in claim 8, wherein said inert solvent is a mixture of water with monohydric or polyhydric alcohols, wherein the monohydric or polyhydric alcohol content of the alcohol/water mixture is 10–90% by weight.

10. The process as claimed in claim 8, wherein said inert solvent is a mixture of water with monohydric or polyhydric alcohols, wherein the monohydric or polyhydric alcohol content of the alcohol/water mixture is 30–70% by weight.

11. The process as claimed in claim 8, wherein said monohydric or polyhydric alcohol is selected from the groups consisting of methanol, ethanol, isopropanol, ethylene glycol, 1,2-propanediol, 1,3-propandiol, and mixtures thereof.

12. The process as claimed in claim 1, wherein said surface postcrosslinking solution is employed in a proportion of 1–20% by weight based on a mass of said polymer.

13. The process as claimed in claim 1, wherein said surface postcrosslinking solution is employed in a proportion of 2.5–15% by weight based on a mass of said polymer.

14. A water-absorbing polymer prepared by the process claimed in claim 1.

15. A hygiene article, packaging material or nonwoven, comprising; the water-absorbing polymer as claimed in claim 14.

* * * * *